United States Patent [19]

Goedert

[11] Patent Number: 4,935,040
[45] Date of Patent: Jun. 19, 1990

[54] MINIATURE DEVICES USEFUL FOR GAS CHROMATOGRAPHY

[75] Inventor: Michel G. Goedert, Ridgefield, Conn.
[73] Assignee: The Perkin-Elmer Corporation, Norwalk, Conn.
[21] Appl. No.: 330,246
[22] Filed: Mar. 29, 1989
[51] Int. Cl.$^5$ .................. B01D 15/08; G01N 30/66
[52] U.S. Cl. ........................ 55/197; 55/208; 55/270; 55/386; 73/23.22; 210/198.3
[58] Field of Search .............. 55/67, 197, 386, 208, 55/270, 274; 73/23.1; 210/198.3

[56] References Cited

U.S. PATENT DOCUMENTS

| | | | |
|---|---|---|---|
| 3,138,948 | 6/1964 | Pfefferle | 73/27 R |
| 3,146,616 | 9/1964 | Loyd | 55/67 X |
| 3,149,941 | 9/1964 | Barnitz et al. | 55/386 |
| 3,319,403 | 5/1967 | Rose et al. | 55/386 |
| 3,449,938 | 6/1969 | Giddings | 55/67 X |
| 3,503,712 | 3/1970 | Sussman | 55/386 X |
| 3,538,744 | 11/1970 | Karasek | 55/67 X |
| 3,630,006 | 12/1971 | Sandoval | 55/386 |
| 3,748,833 | 7/1973 | Karas et al. | 55/197 |
| 3,856,681 | 12/1974 | Huber | 55/386 X |
| 4,116,836 | 9/1978 | DeAngelis | 55/386 X |
| 4,142,400 | 3/1979 | Colla et al. | 73/23 |
| 4,394,263 | 7/1983 | Dosch et al. | 55/386 X |
| 4,471,647 | 9/1984 | Jerman et al. | 73/23.1 X |
| 4,575,424 | 3/1986 | Allington et al. | 55/197 X |

FOREIGN PATENT DOCUMENTS

| | | | |
|---|---|---|---|
| 60-142254 | 7/1985 | Japan | 55/386 |
| 60-229342 | 10/1985 | Japan | 55/386 |
| 61-142462 | 6/1986 | Japan | 55/386 |
| 61-176853 | 8/1986 | Japan | 55/67 |
| 61-233365 | 10/1986 | Japan | 55/386 |
| 61-233366 | 10/1986 | Japan | 55/386 |
| 61-288154 | 12/1986 | Japan | 55/386 |
| 63-098561 | 4/1988 | Japan | 73/23.1 |
| 399780 | 3/1966 | Switzerland | 55/197 |

OTHER PUBLICATIONS

"A Prototype Gas Analysis System Using a Miniature Gas Chromatograph" by J. H. Jerman, S. C. Terry and S. Saadat, Stanford University, Jun. 2, 1980.
"Silicon as a Mechanical Material" by K. E. Peterson, Proc. IEEE 70, 420–457, May 1982.
"A Microminiature Electric-to Fluidic Valve" by M. J. Zdeblick and J. B. Angell, Transductors 87, pp. 827–829 (1987).
"Boron Nitride Mask Structure for X-Ray Lithography" by D. Maydan, G. A. Coguin, H. J. Levinstein, A. K. Sinha and D. N. K. Wang, J. Vac. Sci Technol 16 1959–61 (Nov./Dec.) 1979.

Primary Examiner—Robert Spitzer
Attorney, Agent, or Firm—H. S. Ingham; E. T. Grimes

[57] ABSTRACT

Laminated wafers with channels formed therein define a plurality of gas chromatographic columns in a body, with substantially minimal connecting channels between an injector and a detector. One or more of the columns at a time is selected by valve to be receptive of sample gas. Detector and injector cavities have surfaces with the adsorbent phase utilized in the column being further coated on the surfaces, whereby the detector and injector constitute an integral portion of the gas chromatographic column. A channel is formed between wafers each with grooves that have semicircular cross sections so as to form the channel with a circular cross section. A digital gas injector includes a plurality of chambers with respective measured volumes. Valves select one or more of the chambers at a time to be receptive of sample gas from the common inlet. A detector comprises a body having a passage therein receptive of a first flow consisting of a sample gas mixed into a carrier gas, and alternatively receptive of a second flow consisting of a reference gas. Preferably the first and second flows are oppositely directed by valves alternatively through the passage. Boron or silicon nitride film is utilized in cavities in the body so as to provide a structural component for membranes of the valves and for hot wire detectors.

30 Claims, 6 Drawing Sheets

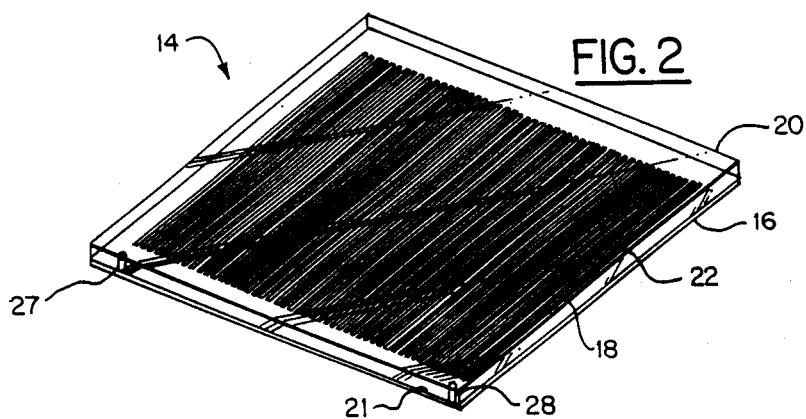
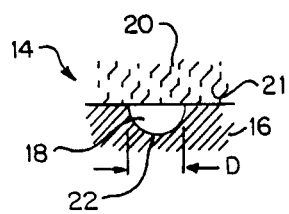
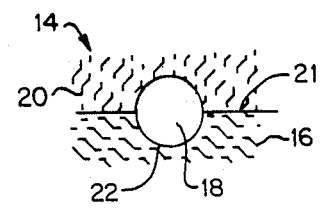
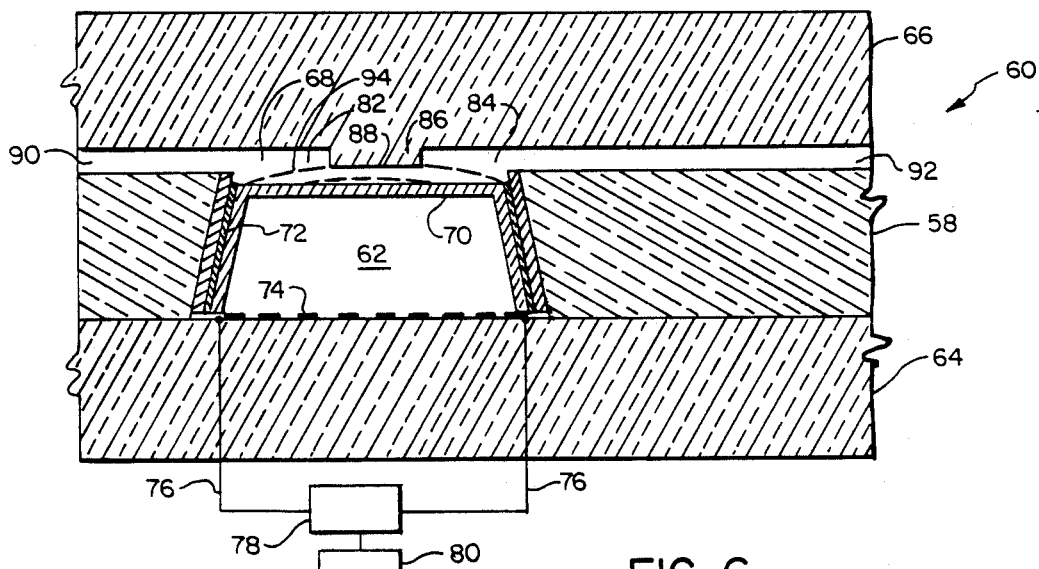

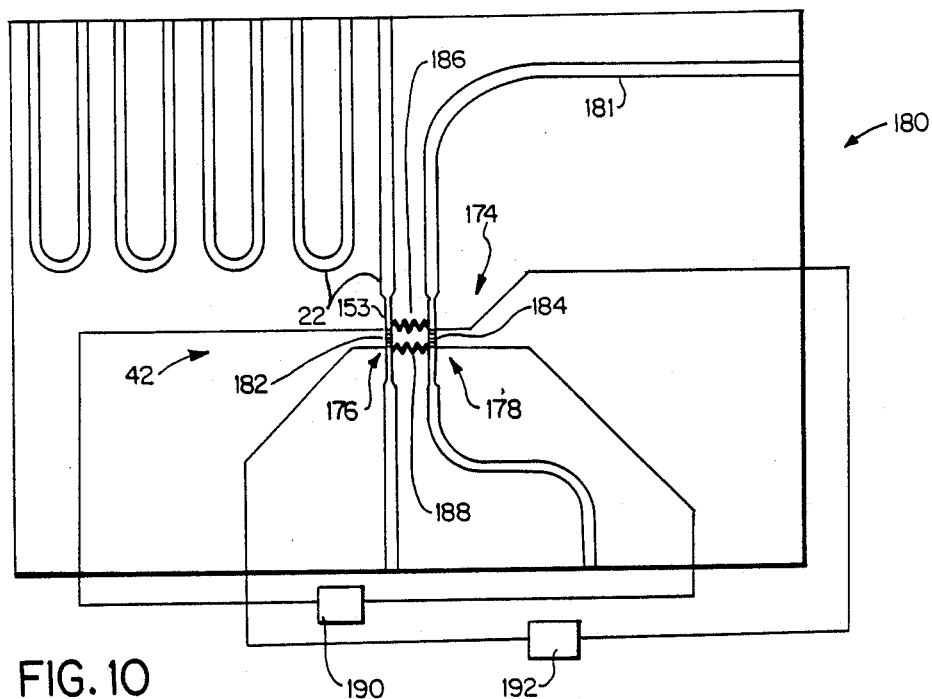
FIG. 10
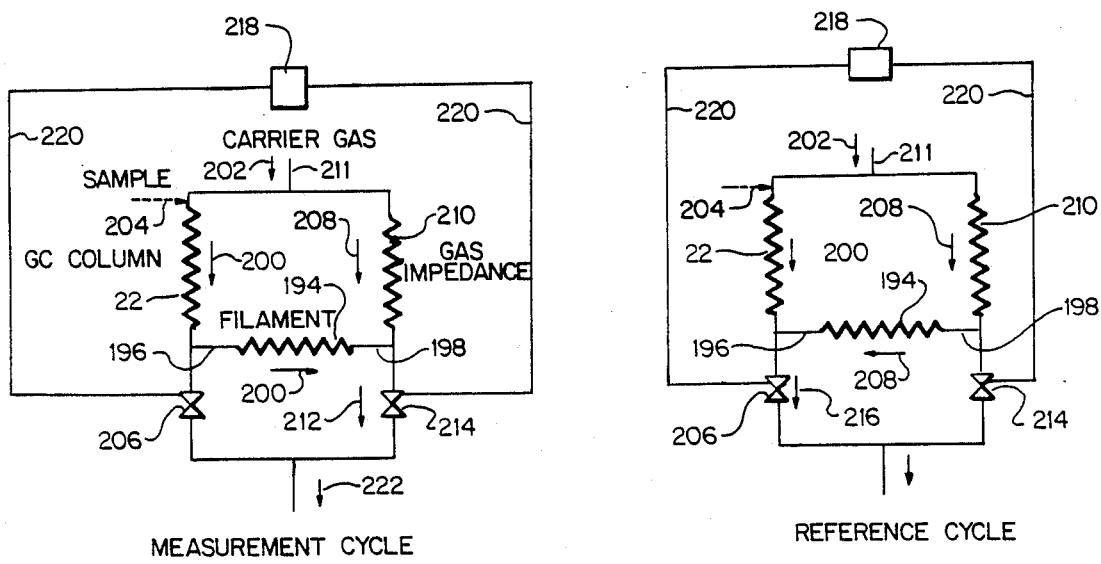
FIG. 11A
FIG. 11B

MINIATURE DEVICES USEFUL FOR GAS CHROMATOGRAPHY

The present invention relates generally to miniature devices and particularly to unitary gas chromatographic devices.

BACKGROUND OF THE INVENTION

Generally, in gas chromatography ("GC"), a sample to be analyzed is introduced as a pulse of gas in a stream of carrier gas into a chromatographic column. A separation process takes place in the column, and at the end of the column the individual components of the sample will emerge more or less separated in time. The individual components separated by the column are detected by continuously monitoring some physical or chemical property of the effluent.

Ideally, each component in the sample emerges from the column at different times so that, at any one time, the gas flowing into the detector is either all carrier gas or a combination of carrier gas and one of the components of the sample. The detector functions by producing a signal related to the change in the intensity of a given characteristic of the gases flowing through it. As each sample component passes through the detector, the output signal varies from the value it has when the detector is full of carrier gas, with the amount of variation depending on the concentration of the sample component and typically being in the form of a spike or peak on a steady signal. A widely used detector is the thermal conductivity detector (also referred to as a hot wire detector or katharometer) which measures the difference between the thermal conductivity of the pure carrier gas and the mixture of the sample component and the carrier gas.

An injector is also part of a GC system, for introducing the short pulse of a sample gas to be analyzed into carrier gas before the column. Conventional injectors involve the use of a syringe for providing a measured volume of sample.

A miniaturized GC system is disclosed in a report "A Prototype Gas Analysis System Using a Miniature Gas Chromatograph" by J. H. Jerman, S. C. Terry and S. Saadat, Stanford University (June 1, 1980), and in an article "Silicon as a Mechanical Material" by K. E. Petersen, Proc. IEEE 70, 420-457 (May 1982). The techniques of integrated electronic circuit processing are utilized to form the main components of a GC system. A capillary column is formed by etching and laminating wafers of silicon and glass. A valve for the injector comprises a mechanical solenoid plunger and a nickel diaphragm. A volume of sample gas is injected through a capillary by computerized coordination of pressures. A hot wire thermal detector is formed with a thin-film nickel resistor on a thin glass membrane in a cavity.

An improved valve for such a system is disclosed in "A Microminiature Electric-to Fluidic Valve" by M. J. Zdeblick and J. B. Angell, Transducers 87, pp 827-829 (1987). The valve utilizes a sealed cavity filled with a liquid. One wall of the cavity is formed with a flexible membrane which can press against a pneumatic nozzle. When the liquid is heated, it's pressure increases, pushing the membrane toward the nozzle, turning it off.

Although the aforementioned background reflects advancements in miniaturized devices including GC systems, further improvements are quite desirable to increase reliability and precision of operation and also to simplify manufacturability of parts. There also are requirements to reduce even further size, weight, and electrical consumption of instruments for applications such as for aerospace where they are at a premium.

Therefore an object of the present invention is to provide an improved unitary device such as for gas chromatography device, particularly a device of the type utilizing a plurality of wafer members laminated together, having increased flexibility, reliability, speed and precision of operation. Further objects are to provide improved components in such a device, including unique gas chromatographic column structures, sample gas injectors, and detectors.

Another object is to provide an improved gas valve in a unitary body. Yet other objects are to provide an improved gas detector system and to provide a unique structural material for a miniature device.

SUMMARY OF THE INVENTION

The foregoing and other objects are achieved by a unitary gas chromatographic device comprising a body formed of a multiplicity of wafer members laminated together. The wafer members have mating surfaces with channels formed therein such as to define a plurality of gas chromatographic columns in the body. The device further comprises injector means disposed in the body for injecting sample gas into the columns. The columns and injector means should be arranged in the body with substantially minimal connecting channels between the injector means and the columns. The device according to a preferred embodiment further comprises selection means disposed in the body for selecting one or more of the columns at a time to be receptive of sample gas from the injector means.

The selection means preferably comprises one or more gas valves. Each valve comprises a portion of the body having therein a first cavity and an adjacent second cavity with an inlet portion and an outlet portion, a membrane disposed in the body so as to separate the first and second bodies, a thermally expandable medium filling the first cavity, heating means for heating the medium to expand the medium such that the membrane is caused to distend into the second cavity, and a protrusion extending into the second cavity to a location proximate the membrane such that the outlet portion is closed off from the inlet portion by the distended membrane and open to the inlet portion when the membrane is non-distended. This control of the heating means operates the membrane as a gas valve.

According to another embodiment, the body further includes a detector cavity therein juxtaposed with the gas outlet of a gas chromatographic column to be receptive of sample gas from the column. The detector cavity has at least one component associated therewith in the detector cavity to provide detector means for detecting a characteristic of the sample gas. The detector cavity and the at least one associated component have collective surfaces thereof in the detector cavity with the adsorbent phase utilized in the column being further coated on the collective surfaces, whereby the detector means constitutes an integral portion of the gas chromatographic column. Preferably the unitary device further comprises injector means juxtaposed with the gas inlet for injecting sample gas into the column, and the adsorbent phase is further coated on at least a portion of the injector surfaces whereby the injector means constitutes a further integral portion of the gas chromatographic column. Preferably the stationary phase is a liquid phase. In a further embodiment, the body is formed of at least two adjacent wafer members laminated together including a first wafer member with a first surface and a second wafer member with a second surface bonded to the first surface. The first surface has therein a first serpentine groove and the second surface has therein a second serpentine groove in alignment with the first groove so as to define a serpentine channel in the body. Desirably the first and second grooves have semicircular cross sections so as to form the channel with a circular cross section.

A gas injector useful for gas chromatography according to the invention comprises a body having therein a plurality of chambers with respective measured volumes. The body further has therein a common gas inlet receptive of sample gas and further has a common gas outlet. The injector further comprises valve means disposed in the body, the valve means being responsive to controller means for selecting one or more of the chambers at a time to be receptive of sample gas from the common inlet. The injector further comprises pressure means for forcing the sample gas from the one or more selected cavities through the outlet. Thus the total of the respective measured volumes of the selected one or more chambers corresponds to a predetermined volume of sample gas forced through the outlet, and different predetermined volumes are provided by control of the valve means.

In another embodiment, a detector for measuring a characteristic of a sample gas comprises a body having a passage therein receptive of a first flow consisting of a sample gas mixed into a carrier gas, the passage alternatively being receptive of a second flow consisting of a reference gas. The detector also comprises valve means for selecting between the first and second flows in the passage. Valve control means oscillate between selecting the first flow or the second flow through the passage. The first and second flows are oppositely directed alternatively through the passage. Detector means produce a time varying signal representing a characteristic of the gas in the passage. Processing means is receptive of the signal for comparing signals for the first and second flows to present a characteristic representing the sample gas.

BRIEF DESCRIPTION OF THE DRAWINGS

FIG. 2 is a perspective view of a paired wafer component of FIG. 1.

FIG. 3 is a magnified cross-section of an embodiment of a column in the component of FIG. 2

FIG. 4 is a magnified cross-section of another embodiment of a column in the component of FIG. 2.

FIG. 6 is a cross-section of a gas valve utilized in the present invention.

FIG. 10 is a plan view of an embodiment for a gas thermal conductivity detector system in a gas chromatographic device according to the present invention.

FIG. 11, consisting of FIGS. 11A and 11B, is a schematic of another embodiment for a gas thermal conductivity detector according to the present invention.

DETAILED DESCRIPTION OF THE INVENTION

The present invention pertains to miniaturized gas circuitry involving various components and combinations of components in a device that may be fabricated especially by techniques similar to electronic device fabrication. The operable components are controlled electronically such as described in the aforementioned report by Jerman et al. For clarity, components are identified in separate headings below.

Planar Columns

Figure 1:
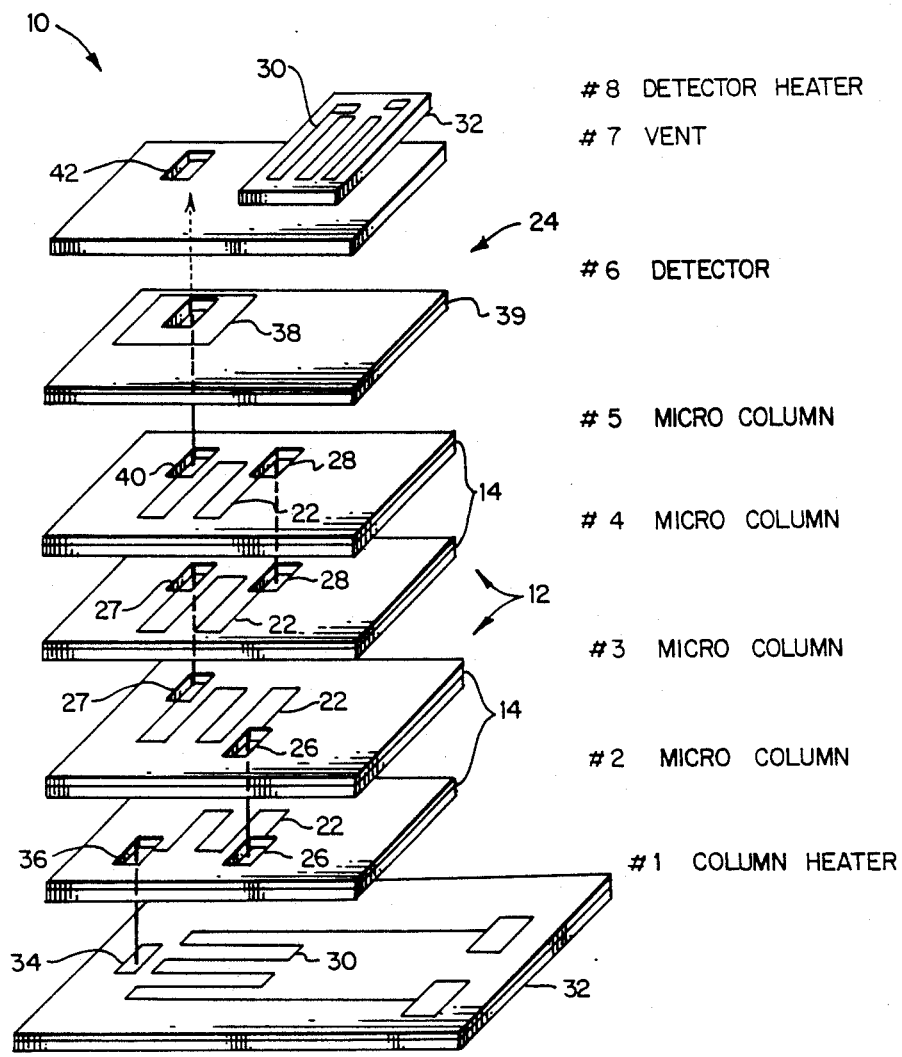
FIG. 1 is an exploded view of a unitary gas chromatographic device according to the present invention.

FIG. 1 shows an exploded view of a unitary gas chromatographic device 10 formed of a multiplicity of wafer members 12 that are all laminated together in the actual device. Initially the wafers are in laminated pairs 14, a laminated pair being shown in FIG. 2. One wafer 16 in the pair is made of silicon or the like which can be etched with conventional techniques, such as described in the aforementioned Stanford report and Petersen article, to form a groove 18 therein such as with a rectangular cross-section or with a semicircular cross section as shown in FIG. 3. For example with a boron nitride mask the groove is etched in a (100) plane of silicon with a mixture of hydrofluoric, nitric, and acetic acids (HNA) in proportions 9:75:30 by vol at 22° C. for 10 minutes. The second wafer 20 is preferably glass or quartz with a thermal expansion coefficient similar to that of the first wafer, for example Pyrex (TM) glass. Bonding of wafers 16,20 at their interface 21 is effected by heating them under a small compressive load to 350° C. for 10 minutes with a DC voltage of 1500 V. The structure 14 is, e.g., 6 mm thick by 5 cm×5 cm, and has a serpentine channel 22 etched therein which, in a coiled or zig-zag form, may be utilized as a gas chromatographic column. The channel may have a cross sectional dimension D (FIG. 3) between 20 and 220 microns, and a depth of approximately half of these thicknesses, with row separations of 2 to 3 times the cross section. All these dimensions are controllable through the photolithographic and etching process.

Alternatively second wafer 20 also has a groove 22 therein in alignment with first groove 18 to define serpentine channel 22. The second groove should be substantially identical to the first groove, for example to provide a circular channel as depicted in FIG. 4. More broadly the channel may be axisymmetrical as desired for providing suitable inside surface area for adsorbsion. Keys (not shown) may be etched in the wafers 16,20 for alignment, or if one or both of the wafers is glass, as in FIG. 2, the two wafers may be aligned visually. If both wafers are silicon, bonding may be effected as described above with a thin layer of silica between.

With reference again to FIG. 1, a plurality of wafer pairs 14 are stacked and laminated together so as to form a unitary body 24 and to generally align a corresponding plurality of chromatographic micro-columns 22 (four shown). Bonding is effected as described above for each pair of wafers. The columns may be of various dimensions and contain selected stationary liquid phases, as required for simple or complex chromatography.

For example, a typical stationary phase may be bonded methyl silicon, or bonded Carbowax (TM), or the like. In a simple form of device 10, planar columns 22 may be linked by connecting channels 26,27,28 directly aligned in pairs to lead perpendicularly through laminated wafers 14. Columns 22 may be connected in series (preferably, as shown) or in parallel by employing columns of different selectivities to optimize complex chromatographic separations. With ten columns and each column being 5 meters long, a total column length of 50 meters or more may be achieved in a single miniature device 5×5×5 cm.

A heating element 30 conventionally formed of nickel film, with a thermostatic control (not shown) may be formed in at least one end wafer member 32. With such a small device very uniform temperature control of a very long column is quite practical, with less than 10 watt of electrical consumption. Compared with conventional means of column heating this is a reduction of almost two orders of magnitude.

An injector device 34 for injecting a sample gas into a carrier gas duct 36 and thence into columns 22 is also integrated into body 24. A detector 38 is provided in a wafer group 39 at outlet 40 of the columns, and the gas exits through a vent 42. Details for preferable injectors and detectors are described below. The injector and detectors should be connected as close together as practical to the columns to substantially minimize any dead volume between. Similarly all connecting channels between individual columns should be minimized. (For clarity the channels are oversized in FIG. 1.) The laminated structure thus described particularly allows such minimum volumes, a highly desirable goal in gas chromatography to minimize peak broadening. Although described herein for gas, devices within the present invention may be utilized for liquids.

Integrated Miniaturized Valves

Figure 5:
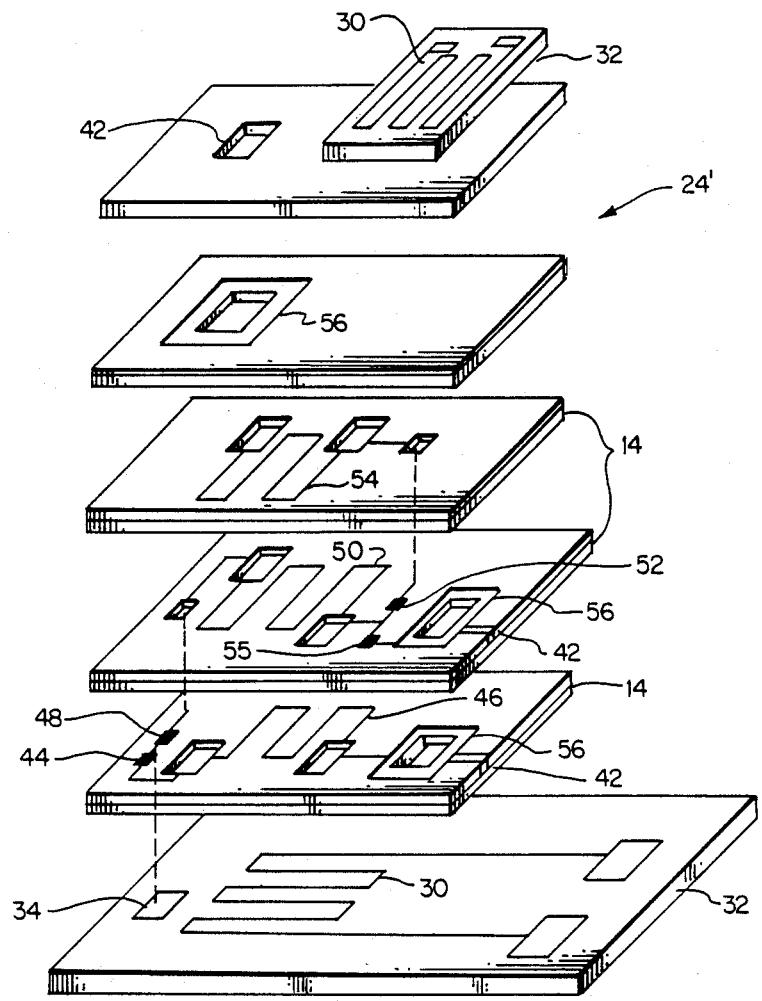
FIG. 5 is an exploded view of a unitary gas chromatographic device according to a further embodiment of the present invention.

According to a further embodiment shown as an example in FIG. 5, gas valves are disposed in a body 24' for selecting one or more of the columns at a time to be receptive of the sample gas. A first injector valve 44 connects injector 34 to a first column 46, and a second injector valve 48 similarly connects the injector to a second column 50. Opening of either valve with the other closed selects a corresponding column 46 or 50 for receiving the sample gas. Opening both valves selects both columns. An intermediate valve 52 is disposed between second column 50 and a third column 54 while another valve 55 bypasses the third column, allowing optional series (tandem) selection of these columns. Other permutations and combinations may conveniently be utilized as desired, such as a single column followed by several columns selectively in parallel. A plurality of detectors 56 with vents 42 may be utilized, with one for each column, to minimize dead volume from each column.

The valves are of the known or desired type for miniature gas devices, for example as taught by Zdbelick et al and shown in FIG. 6. A middle wafer 58 of a laminate 60 has therein a first cavity 62 closed off by a bottom wafer 64. An upper wafer 66 has therein a second cavity 68 adjacent to cavity 62. A membrane 70 is disposed in laminate body 60 so as to separate the first and second cavities. The membrane may be formed as the bottom of a cup-shaped film of aluminum deposited as described in the reference, or may be a film of a nitride or an oxynitride of silicon or boron deposited in the cavity. Other layers 72 of aluminum may be used for bonding the boron nitride to wafer 58. Electrical heating element strips 74 of nickel or the like for operating the valve are also deposited adjacent cavity 62 on bottom wafer 64 and connected by electrical leads 76 to a source 78 of electrical current responsive to a controller 80, the electronics being shown schematically in FIG. 6 but preferably incorporated as integrated electronic circuits into the device such as a solid state relay. Upper cavity 68 is divided into an inlet portion 82 and an outlet portion 84 by a protrusion 86 extending from upper wafer 66 to a surface location 88 proximate membrane 70 but spaced slightly therefrom. An inlet gas passage 90 etched into wafer 66 extends to the inlet cavity and an outlet gas passage 92 extends from the outlet cavity.

Lower cavity 62 is filled with a medium such as liquid methyl chloride as disclosed in Zdbelick et al, which will expand significantly when heated by element 74, preferably by partially vaporizing. The expansion will cause membrane 70 to distend into the upper cavity, as shown by broken lines 94, to a sealing surface at location 88 on protrusion 86 to close off outlet portion 84 from inlet portion 82. Thus in a non-distended, relaxed position the membrane allows gas to flow between the passages, and current to the heating element results in the membrane distending to close off gas flow.

Sample Gas Injector

Figure 8:
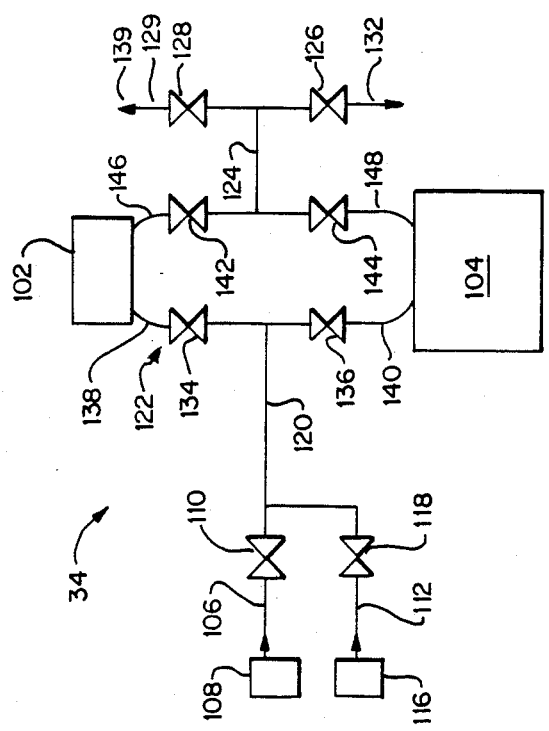
FIG. 8 is a schematic diagram of the injector of FIG. 7.
Figure 7:
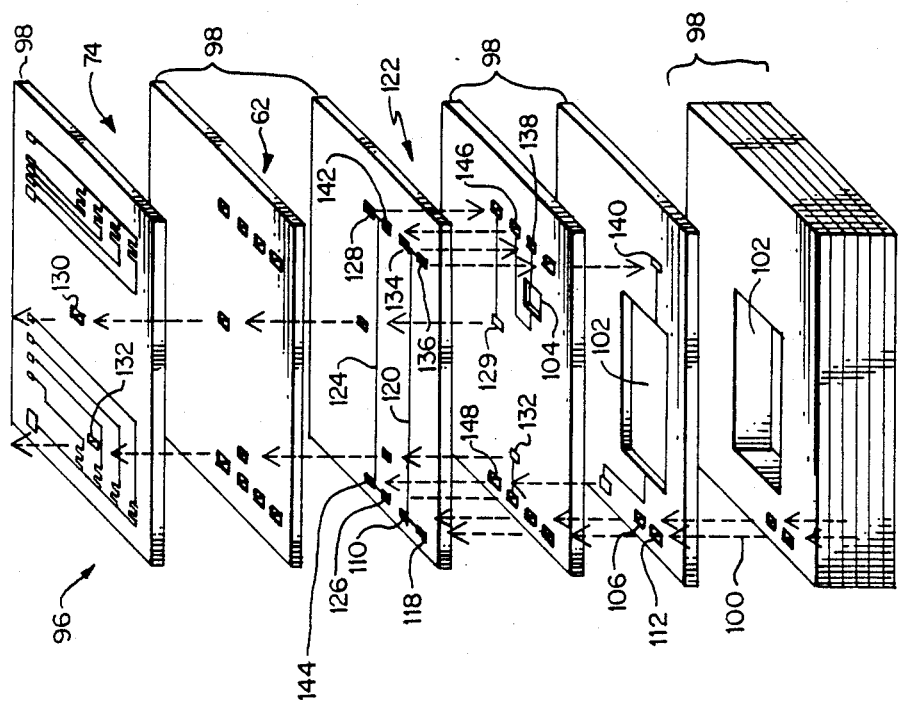
FIG. 7 is an exploded view of a unitary injector according to the present invention.

A laminated body 96 of wafer members 98 forming a gas injector according to the present invention is shown in FIG. 7, with a schematic diagram thereof shown in FIG. 8. Vertical gas flows are shown in FIG. 7 by the dotted lines 100. This body may be a sub-body laminated into the body of FIG. 1 or FIG. 5, at the bottom thereof to provide injector 34. The purpose of this embodiment is to provide an injector for gas chromatography or other such purpose where the volume of sample being injected is variable and selectable by digital control (rather than by analog as for a syringe type of injector). This is achieved by a plurality of chambers, perhaps of different sizes, which are disposed in the body in sufficient quantity to provide for the desired range of volumes. For example, ten cavities each with a volume double that of the preceding one will allow a range of injected volume covered from one to 512. Other parallel or serial arrangements with different increments are possible. For clarity only two chambers 102,104 of different sizes are shown in FIGS. 7 and 8; additional chambers may be selectable in parallel and/or series with these. For example, chambers 102,104 may be 10 microliters and 1000 microliters respectively.

A carrier gas input duct 106 receives carrier gas such as helium or hydrogen on a gas line from a pressurized source 108 (FIG. 8) and terminates at a first valve 110 preferably of the type described above. A sample gas input duct 112 receives sample gas from a container 116 for gas chromatographic analysis and terminates at a second valve 118 in the body. The outputs of these two valves are connected together to a common gas inlet line 120 leading to a plurality of chambers (two shown at 102,104) via associated further valves in a wafer assembly 122. A common gas outlet line 124 from these chambers and valves connect with a third valve 126 and a fourth valve 128. Fourth valve 128 opens (in a downward loop) through ducting 129 to a disposal such as vent 139 to atmosphere or a disposal container. Third valve 126 connects to an output duct 132 which is adapted for gas communication with a point of utilization, such as the columns of FIG. 1 or FIG. 5 for which the duct should be as short as possible in the device. Liquid medium cavities 62 and heating elements 74 for the valves are depicted in the upper two wafers of FIG. 7.

Two chambers of different sizes are etched into some of the internal wafer members. A first chamber 104 may be formed as a small diameter hole in one wafer. A second, larger chamber 102 is formed as a larger hole through several of the wafers as shown in FIG. 7. A pair of valves 134,136 respectively for each chamber 102,104 is disposed between common inlet line 120 and inlet ducts 138,140 to the respective chambers. Each of another pair of valves 142,144 is disposed between each corresponding chamber outlet 146,148 and common outlet line 124. Thus an inlet and an outlet valve is associated with each chamber. Any additional chambers would have similar valves.

A controller (not shown in FIGS. 7,8) selects the valves as required for a chosen sample volume. The controller is preferably an integrated electronic circuit in the device. Variations contemplated include injection of more than one sample and functions such as backflushing.

Detector

Figure 9:
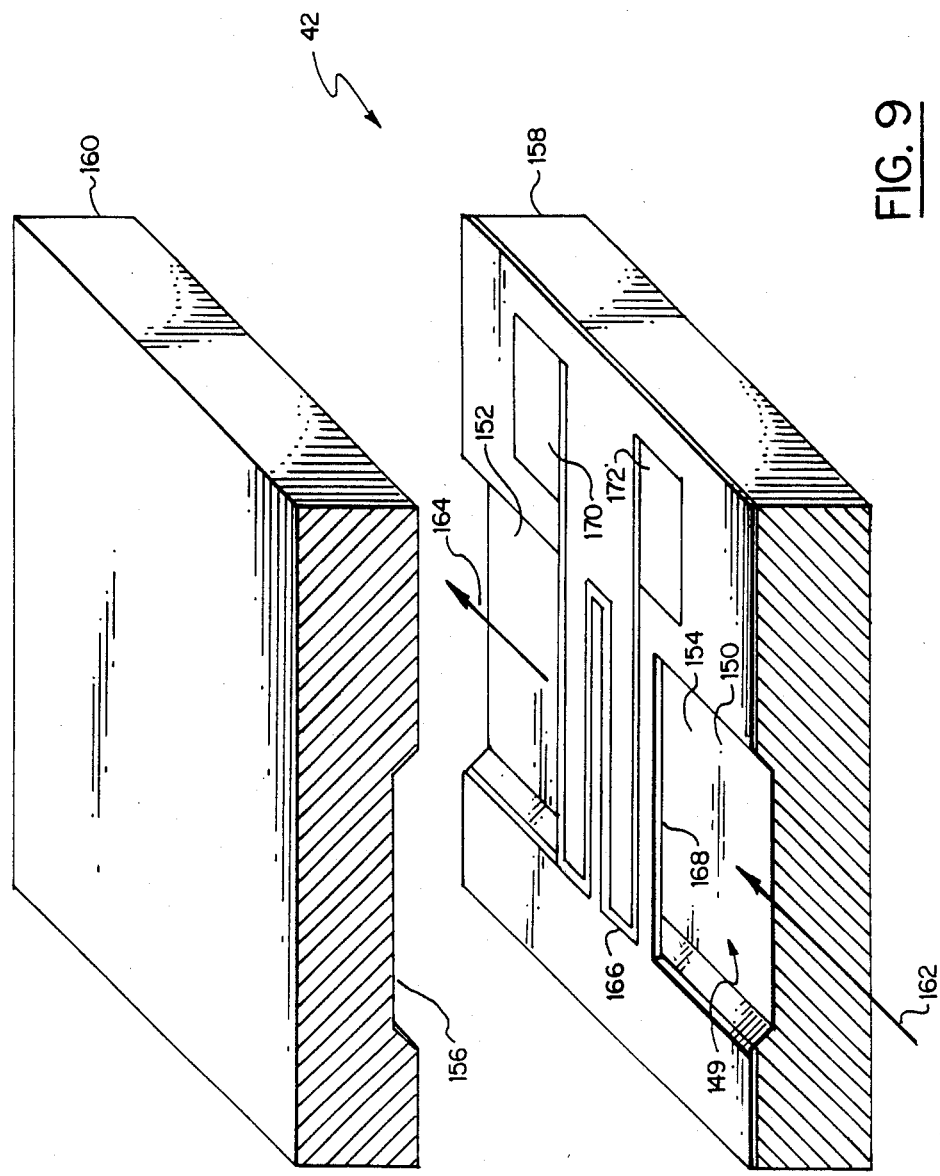
FIG. 9 is an exploded, perspective view of a gas thermal conductivity detector according to the present invention.

FIG. 9 illustrates a hot wire type of gas thermal conductivity detector 42 of the general type disclosed in the Stanford report and preferably utilized in the present invention. A detector cavity 149 with an inlet 150 and an outlet 152 is part of a duct leading from a column 22, and, as explained above and shown in FIG. 10, preferably is juxtaposed with the gas outlet 153 from the column to minimize dead volume and peak widening. The duct is conveniently formed by adjacent grooves 154,156 etched in adjacent wafers 158,160. A carrier gas flowing from the column, as shown by arrows 162,164 has sample gas flowing therein typically in the form of compositional "peaks" resulting from selective adsorption and elution in the stationary phase of the column.

A hot wire electrical resistive element 166 formed conventionally as a thin film of nickel or the like is deposited in a serpentine path on an electrically insulating bridge 168 such as silicon nitride, boron nitride, silicon oxy-nitride or boron oxy-nitride Pyrex (TM) glass, e.g. 1-2 microns thick. The bridge divides grooves 154 and 156. Electrical connections 170,172 for current and voltage measurement are provided for the element. Change in thermal conductivity, associated with eluted sample gas, is detected b the corresponding change of resistance of the thin film resistance and is measured by voltage measurement.

Sensitive voltage measurement may be effected conventionally such as with a Wheatstone bridge 174 as shown in FIG. 10. For example, identical detectors 176,178 are incorporated into the same unitary device 180, proximate each other. Sample gas from column 22 is passed through one detector 176 as described above. A standard gas, typically the carrier gas without sample gas therein, is passed via a duct 181 through the other detector 178. Respective electrical resistive elements 182,184 in the detector cavities, and a third resistor 186 and fourth resistor 188, preferably also contained in the device, form the Wheatstone bridge. A voltage source 190 and an electrometer circuit 192 for the bridge including any associated integrated circuits such as a conventional operational amplifier are further contained in the device. The bridge is preferably operated in a constant temperature mode to avoid thermal runaway but other modes of operation such as constant temperature and constant resistance are also possible. In the constant temperature mode the driving voltage is varied to change the power dissipated by the detector such that the temperature of the filament is held constant.

In a preferred arrangement only one detector is utilized, and the standard gas is alternated through the detector with the gas from the column. A way to do this is disclosed in copending U.S. patent application Ser. No. 200,335 filed May 31, 1988 (Golay) now U.S. Pat. No. 4,856,319 of the present assignee. Briefly, a switching assembly for selectively, alternately filling the detector chamber with carrier gas for a baseline measurement and with effluent for analysis is connected to the detector and includes a gas chamber connected to the detector chamber, a source of carrier gas connected to the gas chamber, and apparatus for selectively heating gas in the gas chamber to cause carrier gas to be expelled from the gas chamber to fill the detection chamber for a baseline measurement and for cooling gas in the gas chamber to withdraw the carrier gas from the detection chamber so as to draw effluent from the column outlet to thereby fill the detection chamber for an analytical measurement. The heating apparatus includes a hot wire filament mounted in the gas chamber and electrically controlled for selective heating. Such a detector arrangement is especially suitable for incorporating into a unitary device of the present invention.

However, for higher performance derived from higher speed in alternating between flows, valving is preferred. Valving also has the advantage to maintain the temperature of the carrier gas and of the sample constant within a cycle. With reference to FIG. 11, the body has a detector passage 194 with a hot wire filament therein, the passage having a first terminal opening 196 and an opposite second terminal opening 198. During a measurement cycle, shown in FIG. 11A, the passage by way of first terminal opening 196 is receptive of a first flow 200 consisting of carrier gas 202 containing an eluted, time varying sample gas 204 from GC column 22. During a reference cycle shown in FIG. 11B, the passage by way of second terminal opening 198 is receptive of a second flow 208 consisting of a reference gas from an impedance 210 of similar gas flow impedance to the column. The reference gas normally should consist of the carrier gas split off from a carrier gas inlet 211. The first and second flows 200,208 are directed alternately and oppositely through passage 194.

To effect the alternate flows, a first valve 214 is connected to selectively vent a combined gas 212 consisting of gas 200 exiting the passage through second terminal 198 and second gas flow 208 bypassing the passage. A second valve 206 is connected to alternatively vent a combined gas 216 consisting of gas 208 exiting the passage through first terminal opening 196 and the first flow 200 bypassing the passage. The first valve is open while the second valve is closed, and vice versa, and an exit gas 222 alternately consists of the combined flows 212 or 216.

Valves 206,214 are, for example, of the type described above for FIG. 6. A valve controller 218 via electrical lines 220 to the valves, alternately opens the first and second valves to oscillate between selecting the first flow or the second flow through the passage. With a detector volume of 20 microliters and, with an oscillator frequency of 10 hertz, peaks with a standard deviation of 0.2 second are readily detected.

A thin film filament ("hot wire") detector is disposed in the passage as described above for FIG. 9 and produces a time varying signal representing the change in thermal conductivity characteristic of the gas in the passage. Processing means receptive of the alternating signals compares the first and second gases 200,208 to present a characteristic representing the sample gas. Valve controller 218 is a conventional pulse generator, and it and the processing means preferably each comprise an integrated electronic circuit contained in the body, thus providing a self contained gas chromatographic device.

Volume of the detector may be between a few microliters and several milliliters. The volume reduction of more than two orders of magnitude from conventional detectors, allows detection of one or two orders of magnitude less sample with improved response time also at least one order of magnitude. The oscillating system with valves is essentially drift-free and has a warm-up time of only a few seconds instead of minutes.

Integrated Column

Generally a gas chromatographic column is coated internally with a stationary phase, which can be an absorbent of a liquid, and as a result of the solution-dissolution process of the solute molecules into and out of the stationary phase, solute retention and resolution in the column are obtained. Preferably, in the present device, this is a liquid phase coating of a type such as described above with respect to Planar Columns, on the inside walls of column 22. According to a preferred embodiment of the present invention, detector cavity 149 (FIG. 9) with associated components including bridge 168 for resistive film 166 is juxtaposed with the gas outlet of column 22 (FIG. 10), and the adsorbent phase is further coated on the collective surfaces of the detector cavity and components. The liquid phase is introduced by filling the column detector and injector train with the selected liquid phase with conventional coating technology used for open tubular columns, using vacuum for backfill in the small sized cavities and channels. The liquid phase is evaporated from the hot wire by electrically bringing the filament to elevated temperature. With this arrangement the detector becomes an integral part of the column, thereby eliminating dead volume and increasing precision of chromatography peaks.

Similarly all the pneumatic lines between the injector and the column the injector means 34 such as described herein (FIG. 8) should also have the adsorbent phase coated thereon and be heated at the column temperature. The output of the injector thus also (or alternatively) constitutes an integral portion of the column, eliminating dead volume after injecting sample gas into the carrier gas column, eliminating dead volume after injecting sample gas into the carrier gas. It may again be appreciated that such features are especially suitable in a unitary device.

Nitride Components

The silicon or boron nitride film is formed with conventional procedures utilized for forming lithography masks for producing integrated electronic circuits, for example as disclosed in an article "Boron Nitride Mask Structure for X-ray Lithography" by D. Maydan, G. A. Coquin, H. J. Levinstein, A. K. Sinha and D. N. K. Wang, J. Vac. Sci Technol. 16, 1959-61 (Nov/Dec 1979). Boron nitride (BN) is deposited on silicon by chemical vapor deposition (CVD). The initial deposited BN has a chemical structure incorporating significant amount of hydrogen (H) as both B—H and N—H. This material is not stable above 300 C and becomes brittle as the residual stress increases. By heating the CVD BN before etching the silicon in dry nitrogen atmosphere at 1100 C for 4 to 8 hours, the CVD BN is transformed into a stable material with a composition of $B_3N$. The boron nitride has most preferably been formed on the (100) plane of single crystal silicon for applications requiring anisotropic etching of V groves but the technique is applicable to any other crystal orientations.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

I claim:

1. A unitary gas chromatographic device comprising a body formed of a multiplicity of wafer members laminated together, the wafer members having mating surfaces with channels formed therein such as to define a plurality of gas chromatographic columns in the body, and further comprising injector means disposed in the body for injecting sample gas into the columns, and one or more gas valves disposed in the body for selecting one or more of the columns at a time to be receptive of the sample gas from the injector means.

2. A device according to claim 1 wherein each valve comprises a portion of the body having therein a first cavity and an adjacent second cavity with an inlet portion and an outlet portion, a membrane disposed in the body so as to separate the first and second bodies, a thermally expandable medium filling the first cavity, heating means for heating the medium to expand the medium such that the membrane is caused to distend into the second cavity, and a protrusion extending into the second cavity to a location proximate the membrane such that the outlet portion is closed off from the inlet portion by the distended membrane and open to the inlet portion when the membrane is non-distended, the whereby control of the heating means operates the membrane as a gas valve.

3. A device according to claim 2 wherein the membrane is formed of a nitride of boron or silicon.

4. A gas chromatographic device comprising a body having therein a gas chromatographic column with a gas inlet and a gas outlet, the column having inside column walls with an adsorbent phase being coated thereon, the body further having a detector cavity therein juxtaposed with the gas outlet to be receptive of sample gas from the column, the detector cavity having at least one component associated therewith in the detector cavity to provide detector means for detecting a characteristic of the sample gas, and the detector cavity and the at least one associated component having collective surfaces thereof in the detector cavity with an adsorbent phase being further coated on the collective surfaces, whereby the detector means constitutes an integral portion of the gas chromatographic column.

5. A device according to claim 4 wherein the body is formed of at least two wafer members having mating surfaces laminated together with at least one such surface having a serpentine groove therein to define the gas chromatographic column in the body.

6. A device according to claim 4 wherein at least one of the wafer members is formed of single crystal silicon.

7. A device according to claim 4 wherein the absorbent phase is a liquid phase.

8. A device according to claim 4 wherein the detector cavity has a cavity inlet receptive of a sample gas in a carrier gas and a cavity outlet for passage of the gas through the detector cavity and the detector means comprises an electrical resistive element extending laterally through the detector cavity and being receptive of a heating current and of a voltage measuring device, the voltage being a measure of thermal conductivity of the sample gas.

9. A device according to claim 8 wherein the detector means further comprises an electrically insulating bridge extending laterally through the detector cavity, and the resistive element consists of a thin film resistor supported by the bridge.

10. A device according to claim 9 wherein the bridge is formed of a nitride of boron or silicon.

11. A device according to claim 8 further comprising a second detector including a second resistive element, the second detector being substantially identical to and proximate the first detector and being receptive of a reference gas, the first and second resistive elements being components of a Wheatstone bridge circuit.

12. A gas chromatographic device comprising a body having therein a gas chromatographic column with a gas inlet and a gas outlet, the column having inside column walls with an adsorbent phase being coated thereon, the body further having a detector cavity therein juxtaposed with the gas outlet to be receptive of sample gas from the column, the detector cavity having at least one component associated therewith in the detector cavity to provide detector means for detecting a characteristic of the sample gas, and the detector cavity and the at least one associated component having collective surfaces thereof in the detector cavity with an adsorbent phase being further coated on the collective surfaces whereby the detector means constitutes an integral portion of the gas chromatographic column, the device further comprising injector means juxtaposed with the gas inlet for injecting sample gas into the column, the injector means being formed of at least one injector cavity in the body, the at least one cavity having injector surfaces thereof with an adsorbent phase being further coated on at least a portion of the injector surfaces whereby the injector means constitutes a further integral portion of the gas chromatographic column.

13. A device according to claim 12 further comprising at least one respective valve component in the at least one injection cavity for valving the sample gas into the column, the at least one respective valve component having valve surfaces thereof in the at least one injection cavity with the adsorbent phase being further coated on the valve surfaces.

14. A device according to claim 13 wherein each valve comprises a portion of the body having therein a first cavity and an adjacent second cavity with an inlet portion and an outlet portion, a membrane disposed in the body so as to separate the first and second bodies, a thermally expandable medium filling the first cavity, heating means for heating the medium to expand the medium such that the membrane is caused to distend into the second cavity, and a protrusion extending into the second cavity to a location proximate the membrane such that the outlet portion is closed off from the inlet portion by the distended membrane and open to the inlet portion when the membrane is non-extended, whereby control of the heating means operates the membrane as a gas valve.

15. A device according to claim 14 wherein the membrane is formed of a nitride of boron or silicon.

16. A gas chromatographic device comprising a body having therein a gas chromatographic column with a gas inlet and a gas outlet, the column having inside column walls with an adsorbent phase being coated thereon, the device further comprising injector means juxtaposed with the gas inlet for injecting sample gas into the column, the injector means being formed of at least one injector cavity in the body, the at least one cavity having injector surfaces thereof with an adsorbent phase being further coated on at least a portion of the injector surfaces whereby the injector means constitutes an integral portion of the gas chromatographic column.

17. A device according to claim 16 further comprising at least one respective valve component in the at least one injection cavity for valving the sample gas into the column, the at least one respective valve component having valve surfaces thereof in the at least one injection cavity with the adsorbent phase being further coated on the valve surfaces.

18. A device according to claim 16 wherein the body is formed of at least two wafer members having mating surfaces laminated together with at least one such surface having a serpentine groove therein to define the gas chromatographic column in the body.

19. A device according to claim 18 wherein at least one of the wafer members is formed of single crystal silicon.

20. A device according to claim 16 wherein the adsorbent phase is a liquid phase.

21. A unitary gas chromatographic device comprising a body formed of a multiplicity of wafer members laminated together, the wafer members having mating surfaces with channeling formed therein such as to define in the body a gas chromatographic column having a column inlet and a column outlet and further define in the body an impedance channel having an impedance inlet and an impedance outlet, the impedance channel having a resistance to gas flow similar to that of the column, the body further having therein a carrier gas duct receptive of a source of carrier gas, the carrier gas duct having a first branch connected to provide a carrier gas flow into the column inlet and a second branch connected to provide a reference gas flow into the impedance inlet, the device further comprising injector means disposed in the body for injecting sample gas into the first carrier gas flow proximate the column inlet, the body further having a detector passage therein having a first terminal connected to the column outlet and a second terminal connected to the impedance outlet, the device further comprising a first valve in the body connected between the first terminal and a vent, a second valve in the body connected between the second terminal and a vent, valve control means for alternatively opening the first and second valves to oscillate between selecting the first flow or the second flow through the passage while simultaneously venting directly the second or first flow correspondingly, while bypassing the passage, detector means disposed in the passage for producing a time varying signal representing a characteristic of the gas in the passage, and processing means receptive of the signal for comparing signals for the first and second flows to present a differential characteristic representing the sample gas.

22. A unitary device according to claim 21 wherein the valve control means and the processing means comprise integrated electronic circuitry contained in the body.

23. A gas injector useful for gas chromatography, comprising a body having therein a plurality of chambers with respective measured volumes, the body further having therein a common gas inlet receptive of sample gas and further having a common gas outlet, the injector further comprising valve means disposed in the body, the valve means being responsive to controller means for selecting one or more of the chambers at a time to be receptive of sample gas from the common inlet, and the injector further comprising pressure means for forcing the sample gas from the one or more selected cavities through the outlet, whereby the total of the respective measured volumes of the selected one or more chambers corresponds to a predetermined volume of sample gas forced through the outlet, and different predetermined volumes are provided by control of the valve means.

24. An injector according to claim 23 wherein the valve means comprises a multiplicity of valves each being disposed between the inlet and a respective chamber and a further multiplicity of further valves each being disposed between each respective chamber and the outlet.

25. An injector according to claim 24 wherein the body further has therein a carrier gas input duct receptive of a source of carrier gas and terminating at a first valve disposed in the body, a sample gas input duct receptive of a source of sample gas and terminating at a second valve disposed in the body, a venting duct commencing at a third valve disposed in the body and being open to disposal, and an output duct commencing at a fourth valve disposed in the body and being adapted for gas communication with a point of utilization, the first and second valves having a first common gas connection in the body with the inlet, and the third and fourth valves having a second common gas connection in the body with the outlet.

26. An injector according to claim 24 wherein each valve comprises a portion of the body having therein a first cavity and an adjacent second cavity with an inlet portion and an outlet portion, a membrane disposed in the body so as to separate the first and second bodies, a thermally expandable medium filling the first cavity, heating means for heating the medium to expand the medium such that the membrane is caused to distend into the second cavity, and a protrusion extending into the second cavity to a location proximate the membrane such that the outlet portion is closed off from the inlet portion by the distended membrane and open to the inlet portion when the membrane is non-extended, whereby control of the heating means operates the membrane as a gas valve.

27. An injector according to claim 26 wherein the membrane is formed of a nitride of boron or silicon.

28. A detector for measuring a characteristic of a sample gas, comprising a body having a passage therein receptive of a first flow consisting of a sample gas mixed into a carrier gas, the passage alternatively being receptive of a second flow consisting of a reference gas, the detector further comprising valve means for selecting between the first and second flows in the passage, valve control means for controlling the valve means to oscillate between selecting the first flow or the second flow through the passage, detector means for producing a time varying signal representing a characteristic of the gas in the passage, and processing means receptive of the signal for comparing signals for the first and second flows to present a characteristic representing the sample gas.

29. A detector according to claim 28 wherein the passage has a first terminal opening receptive of the first flow and an opposite second terminal opening receptive of the second flow, whereby the first and second flows are oppositely directed through the passage, and the valve means comprises a first valve connected to selectively vent gas exiting the passage through the first terminal while the second flow is in the passage, and a second valve connected to alternatively vent gas exiting the passage through the second terminal opening while the first flow is in the passage.

30. A detector according to claim 29 wherein the first and second flows are flowed continuously at similar pressures, so that while the second flow is being vented from the passage through the first valve the first flow is simultaneously being vented directly through the first valve while bypassing the passage, and while the first flow is being vented from the passage through the second valve the second flow is being simultaneously vented directly through the second valve while bypassing the passage.

* * * * *